United States Defensive Publication [19] (H) [11] T101,805

Lamberti [43] May 4, 1982

[54] METHOD FOR PRODUCING ALKALI METAL SALTS OF CARBOXYMETHYLOXYSUCCINIC ACID

[76] Inventor: Vincent Lamberti, 11 Holly Dr., Upper Saddle River, N.J. 07458

[21] Appl. No.: 283,573

[22] Filed: Jul. 13, 1981

Related U.S. Application Data

[63] Continuation-in-part of Ser. No. 157,615, Jun. 9, 1980, abandoned, which is a continuation of Ser. No. 960,807, Nov. 15, 1978, abandoned.

[51] Int. Cl.[3] ..... C07C 51/41

[52] U.S. Cl. ..... 562/583

[57] ABSTRACT

An improved method for the conversion of an alkaline earth metal carboxymethyloxysuccinate to a trialkali metal carboxymethyloxysuccinate is disclosed wherein a mixture of alkali metal carbonates and bicarbonates are utilized to precipitate the alkaline earth metal as an insoluble carbonate. The amount of alkali metal carbonate/bicarbonate mixture utilized corresponds to a 1–6% molar excess over the number of moles of alkaline earth metal ion present. The pH of the reaction medium during precipitation is maintained in the range of about 10 to 11.5, preferably 10.6 to 11.0, and the temperature, between 80° and 100° C., preferably 90°–100° C. After separation of the insoluble alkaline earth carbonate, there is obtained a solution of the trialkali metal carboxymethyloxysuccinate containing a low calcium level, namely less than about 0.2% basis the percent of trialkali metal carboxymethyloxysuccinate present.

9 Claims, No Sheets Drawing,

17 Pages Specification

The file of this unexamined application may be inspected and copies thereof may be purchased (849 O.G. 1221, Apr. 9, 1968).